United States Patent [19]

Lafon

[11] Patent Number: 4,774,248

[45] Date of Patent: Sep. 27, 1988

[54] METHODS OF TREATING DEPRESSION AND DEPRESSIVE STATES USING 5-PHENYL-1,4,5,6-TETRAHYDROPYRIMIDINE DERIVATIVES

[75] Inventor: Louis Lafon, Paris, France

[73] Assignee: Societe anonyme dite: Laboratoire L. Lafon, Maisons Alfort, France

[21] Appl. No.: 941,158

[22] Filed: Dec. 12, 1986

[30] Foreign Application Priority Data

Dec. 13, 1985 [FR] France ............................. 85 18462
Mar. 14, 1986 [FR] France ............................. 86 03644

[51] Int. Cl.$^4$ .................. A61K 31/505; C07D 239/06
[52] U.S. Cl. .................... 514/269; 514/256; 544/242; 544/298; 544/335
[58] Field of Search .............. 544/298, 242, 335; 514/256, 269

[56] References Cited

U.S. PATENT DOCUMENTS

| | | | |
|---|---|---|---|
| 4,001,232 | 1/1977 | Groegler et al. | 544/242 |
| 4,258,186 | 3/1981 | Schott et al. | 544/253 |
| 4,281,126 | 7/1981 | Oude Alink | 544/242 |
| 4,404,302 | 9/1983 | Gupta et al. | 524/100 |
| 4,455,426 | 7/1984 | Meyer et al. | 544/253 |

FOREIGN PATENT DOCUMENTS

2601137 7/1986 Fed. Rep. of Germany .

OTHER PUBLICATIONS

R. W. Brimblecombe, Br. J. Pharmac. (1969) 37, 425-435.
W. H. Davies et al, J. Chem. Soc., 1945, 347-354.
Van der Stoel et al, J. Heterocylic Chem, 17, 1617 (1980).
Chemical Abstracts, 77, p. 19 (1972) Abstract No. 70055k.
Chemical Abstracts, 97, p. 712 (1982) Abstract No. 162920e.
D. G. Upshall, Teratology, vol. 5, pp. 287-294.

*Primary Examiner*—Donald G. Daus
*Assistant Examiner*—Diana G. Rivers
*Attorney, Agent, or Firm*—Kuhn and Muller

[57] ABSTRACT

The present invention relates to new derivatives selected from the group comprising:
(i) the 5-phenylhydropyrimidines of the formula:

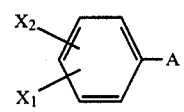

(I)

in which:
$X_1$ and $X_2$, which are identical or different, each represent H, F, Cl, Br or $CF_3$, and
A represents a polyhydropyrimidinyl group of the structure:

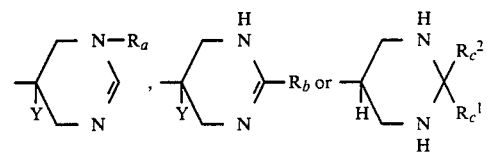

in which:
Y represents H or OH,
$R_a$ represents a $C_1$-$C_4$ alkyl group or a $C_2$-$C_5$ alkanoyl group, it being possible for $R_a$ to represent the hydrogen atom when at least one of the groups $X_1$, $X_2$ and Y is different from H,
$R_b$ represents a $C_1$-$C_3$ alkyl group, and
$R_c^1$ and $R_c^2$, which are identical or different, each represent the hydrogen atom or a $C_1$-$C_3$ alkyl group; and
(ii) their addition salts.

The said derivatives are useful as pharmaceuticals.

3 Claims, No Drawings

METHODS OF TREATING DEPRESSION AND DEPRESSIVE STATES USING 5-PHENYL-1,4,5,6-TETRAHYDROPYRIMIDINE DERIVATIVES

The present invention relates to 5-phenyl-1,4,5,6-tetrahydropyrimidine derivatives as novel industrial products. It also relates to the method for the preparation of these products and their use in therapy, especially as antidepressants for the central nervous system (CNS) and/or sedatives.

From the article by D. G. UPSHALL, Teratology, 5 (No. 3), pages 287–294, (1972), it is known that phenyl-1,4,5,6-tetrahydropyrimidine derivatives, in which the phenyl group is located in the 2, 3 (sic), 4, 5 or 6 position [see Table 1, page 288, and page 289, right-hand column, lines 22–26], have been prepared and tested for possible teratogenic properties on chicken embryos.

Table 1 on page 288 of the said article includes a large number of errors and refers to compounds which clearly cannot be synthesized, in particular compounds Nos. 6–9 and 21. The 1,4,5,6-tetrahydropyrimidines carrying the following substituents are mentioned among the compounds which can actually be prepared: 2-phenyl (cf. compound No. 2, which is described as teratogenic), 4-phenyl (cf. compound No. 10), 4-(4-chlorophenyl) (cf. compound No. 18), 2-methyl-4-phenyl (cf. compound No. 22) and 6-phenyl (cf. compound No. 23).

In other words, the above-mentioned article by D. G. UPSHALL does not describe the compounds according to the invention, of the formula I below, or their use in therapy as substances which act on the CNS. At most, this article refers to the absence of teratogenic effects on chicken embryos of an isomer (the said compound No. 18 mentioned above) of a product according to the invention (CRL 41 336, the subject of Example 1 below).

According to the invention, novel 5-phenyl-1,4,5,6-tetrahydropyrimidine derivatives are recommended which are selected from the group comprising:

(i) the 5-phenylhydropyrimidines of the formula:

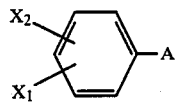

in which:

$X_1$ and $X_2$, which are identical or different, each represent H, F, Cl, Br or $CF_3$, and A represents a polyhydropyrimidinyl group of the structure:

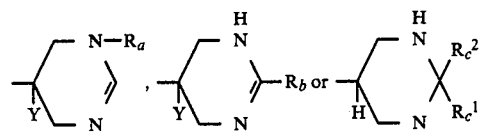

in which:

Y represents H or OH, $R_a$ represents a $C_1$–$C_4$ alkyl group or a $C_2$–$C_5$ alkanoyl group, it being possible for $R_a$ to represent the hydrogen atom when at least one of the groups $X_1$, $X_2$ and Y is different from H, $R_b$ represents a $C_1$–$C_3$ alkyl group, and $R_c^1$ and $R_c^2$, which are identical or different, each represent the hydrogen atom or a $C_1$–$C_3$ alkyl group; and (ii) their addition salts.

This teaching therefore includes:

the 5-phenyl-1,4,5,6-tetrahydropyrimidines, unsubstituted in the 2-position of the hydropyrimidinyl group, of the formula:

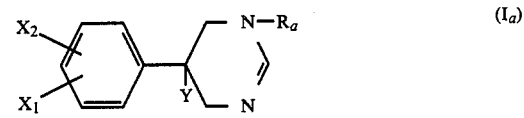

(in which $X_1$, $X_2$, Y and $R_a$ are defined as indicated above in the formula I) and their addition salts, and the 2-alkyl-5-phenyl-1,4,5,6-tetrahydropyrimidines of the formula:

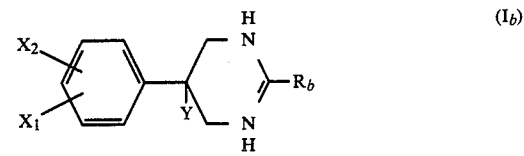

(in which $X_1$, $X_2$, Y and $R_b$ are defined as indicated above in the formula I) and their addition salts, and the 5-phenyl-1,2,3,4,5,6-hexahydropyrimidines of the formula:

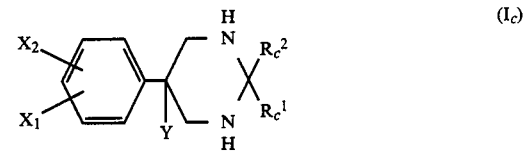

(in which $X_1$, $X_2$, Y, $R_c^1$ and $R_c^2$ are defined as indicated above in the formula I) and their addition salts.

Addition salts are understood here as meaning, on the one hand, the acid addition salts obtained by reacting a free base of the formula I with a mineral or organic acid, and, on the other hand, the ammonium salts. Among the acids which can be used to form salts with the free bases of the formula I, hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular. Among the compounds making it possible to obtain ammonium salts, $CH_3I$ and $CH_3Cl$ may be mentioned in particular. In general, the salts with acids are preferred to the ammonium salts.

The radicals $CH_3$, $CH_2CH_3$, $CH(CH_3)_2$ and $C(CH_3)_3$ may be mentioned in particular among the alkyl groups which are covered by the definition of the group $R_a$ and which are suitable according to the invention, the preferred alkyl groups being $CH_3$, $CH_2CH_3$ and $CH(CH_3)_2$.

$COCH_3$, $COCH_2CH_3$, $COCH_2CH(CH_3)_2$, $COCH(CH_3)_2$, $COC(CH_3)_3$ and $COCH_2CH_2CH_3$ may be mentioned among the alkanoyl groups which are covered by the definition of the group $R_a$ and which are suitable according to the invention, the preferred alkanoyl group according to the invention being COCH₃.

The groups $X_1$ and $X_2$, which can be identical or different, each represent the hydrogen atom, a halogen atom (such as F, Cl or Br) or the trifluoromethyl group, the preferred halogen atoms being F and Cl. In practice, when the phenyl nucleus is substituted, $X_1$ is particularly preferably 3-CF₃ or (especially) 4-Cl or 2-F and $X_2$ is particularly preferably H.

As indicated above, $R_a$ can represent the hydrogen atom when at least one of the substituents $X_1$, $X_2$ and Y is different from H. $R_a$ will advantageously be different from H if, simultaneously, (i) Y=H, (ii) $X_2$=H and (iii) $X_1$=H or 4-Cl.

The groups CH₃, CH₂CH₃, CH₂CH₂CH₃ and CH(CH₃)₂ may be mentioned in particular among the groups $R_b$, $R_c^1$ and $R_c^2$ which are suitable according to the invention, the preferred alkyl group here being CH₃. In practice, for the 1,2,3,4,5,6-hexahydropyrimidinyl compounds, $R_c^1$ and $R_c^2$ are preferably the same alkyl group, especially CH₃, rather than representing the hydrogen atom.

Again in practice, preference is generally given to the compounds of the formula I in which only one of the phenyl and hydropyrimidinyl rings is substituted, rather than to the compounds of the formula I in which both the said rings are substituted.

A number of typical compounds according to the invention have been collated in Tables $I_a$, $I_b$ and $I_c$ below.

TABLE $I_a$

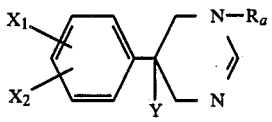

| PRODUCT | CODE NO. | $X_1$ | $X_2$ | Y | $R_a$ |
|---|---|---|---|---|---|
| Ex. 1(a) | CRL 41 336 | 4-Cl | H | H | H |
| Ex. 2(a) | CRL 41 337 | H | H | H | CH₃ |
| Ex. 3(b) | — | 3-Cl | H | H | H |
| Ex. 4(b) | — | 2-Cl | H | H | H |
| Ex. 5(a) | — | 4-Cl | H | H | CH₃ |
| Ex. 6(a) | CRL 41 329 | 2-F | H | H | H |
| Ex. 7(a) | CRL 41 378 | H | H | H | COCH₃ |
| Ex. 8(a) | CRL 41 382 | H | H | OH | H |
| Ex. 9(a) | — | 3-Cl | 4-Cl | H | H |
| Ex. 10(a) | — | 3-Cl | 4-Cl | OH | H |
| Ex. 11(c) | — | 3-Cl | 5-Cl | H | H |
| Ex. 12(a) | — | 3-Cl | 5-Cl | H | CH₃ |
| Ex. 13(a) | — | 2-Br | H | OH | H |
| Ex. 14(b) | — | 3-CF₃ | H | H | H |
| Ex. 15(a) | — | 3-CF₃ | H | H | CH(CH₃)₂ |

Notes
(a): hydrochloride
(b): methanesulfonate
(c): fumarate

TABLE $I_b$

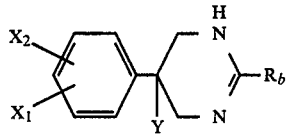

| PRODUCT | CODE NO. | $X_1$ | $X_2$ | Y | $R_b$ |
|---|---|---|---|---|---|
| Ex. 16(a) | CRL 41 352 | H | H | H | CH₃ |
| Ex. 17(a) | — | 4-Cl | H | H | CH₃ |
| Ex. 18(b) | — | 2-F | H | H | CH₃ |
| Ex. 19(c) | — | 3-CF₃ | H | H | CH₃ |
| Ex. 20(b) | — | H | H | OH | CH₃ |

TABLE $I_{b\text{-continued}}$

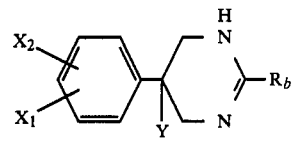

| PRODUCT | CODE NO. | $X_1$ | $X_2$ | Y | $R_b$ |
|---|---|---|---|---|---|
| Ex. 21(a) | — | 3-Cl | 4-Cl | OH | CH₂CH₃ |

Notes
(a): hydrochloride
(b): methanesulfonate
(c): fumarate

TABLE $I_c$

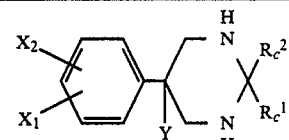

| PRODUCT | CODE NO. | $X_1$ | $X_2$ | Y | $R_c^1$ | $R_c^2$ |
|---|---|---|---|---|---|---|
| Ex. 22(a) | CRL 41 330 | 2-F | H | H | CH₃ | CH₃ |
| Ex. 23(a) | — | H | H | H | CH₃ | CH₃ |
| Ex. 24(c) | CRL 41 365 | H | H | OH | CH₃ | CH₃ |
| Ex. 25(a) | — | 4-Cl | H | H | CH₃ | CH₃ |
| Ex. 26(b) | — | 3-Cl | 4-Cl | H | CH₂CH₃ | CH₂CH₃ |
| Ex. 27(b) | — | 4-Cl | H | OH | CH₃ | CH₃ |
| Ex. 28(a) | CRL 41 355 | H | H | H | H | H |

Notes
(a): dihydrochloride
(b): dimethanesulfonate
(c): free base

The products of the formula I which are preferred on account of their neuropsychopharmacological properties are:

in Table $I_a$ 1-methyl-5-phenyl-1,4,5,6-tetrahydropyrimidine and its acid addition salts such as the hydrochloride, and especially 5-(2-fluorophenyl)-1,4,5,6-tetrahydropyrimidine and its acid addition salts such as the hydrochloride, 1-acetyl-5-phenyl-1,4,5,6-tetrahydropyrimidine and its acid addition salts such as the hydrochloride, and 5-hydroxy-5-phenyl-1,4,5,6-tetrahydropyrimidine and its acid addition salts such as the hydrochloride;

in Table $I_b$ 2-methyl-5-phenyl-1,4,5,6-tetrahydropyrimidine and its acid addition salts such as the hydrochloride; and in Table $I_c$ 2,2-dimethyl-5-(2-fluorophenyl)-1,2,3,4,5,6,-hexahydropyrimidine and its salts with acids, such as the dihydrochloride, and especially 2,2-dimethyl-5-phenyl-1,2,3,4,5,6-hexahydropyrimidine and its acid addition salts such as the dihydrochloride.

The compounds according to the invention can be prepared according to a method known per se by the application of conventional reaction mechanisms.

The method recommended here consists in:

(a) reacting a 2-phenylpropane-1,3-diamine of the formula:

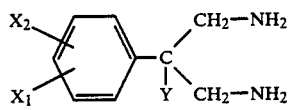 (II)

in which Y, X₁ and X₂ are defined as indicated above, with a reagent selected from the group comprising:
(i) the alkyl formates of the formula:

 (III$_a$)

in which Alk represents a $C_1$–$C_3$ lower alkyl group (preferably $CH_2CH_3$), to give, by cyclization, a compound of the formula I$_a$ in which R$_a$ is H;
(ii) the alkylamidines of the formula:

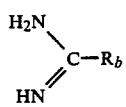 (III$_b$)

in which R$_b$ is defined as indicated above, to give, by cyclization, a compound of the formula I$_b$; and
(iii) the aldehydes and ketones of the formula:

 (III$_c$)

in which R$_c^1$ and R$_c^2$ are defined as indicated above, to give, by cyclization, a compound of the formula I$_c$; and, if necessary,
(b) reacting the said derivative of the formula I$_a$ in which R$_a$ is H with a reagent selected from the group comprising alkylating agents and acylating agents, to give a compound of the formula I$_a$ in which R$_a$ is a $C_1$–$C_4$ alkyl group or, respectively, a $C_2$–$C_5$ alkanoyl group.

Useful information relating to the procedure for carrying out this method for the synthesis of the compounds of the formulae I$_a$, I$_b$ and I$_c$ is given below.

Synthesis of the Compounds of the Formula I$_c$

The reaction of stage (a) is carried out for at least 2 h using proportions of at least one mol of III$_a$ per mol of II. The reaction of II with III$_a$ is advantageously carried out first for 2.5–3.5 h at 100° C. under atmospheric pressure and then for 1 to 5 h at a temperature of 100° to 160° C. under reduced pressure.

The alkylation of stage (b) is carried out by a method known per se. Advantageously, it is recommended here to use a $C_1$–$C_4$ alkyl iodide as the alkylating agent to give the derivatives of the formula I$_a$ in which R$_a$ is a $C_1$–$C_4$ alkyl group. Even more advantageously, to prepare the compounds in which R$_a$=CH$_3$, CH$_2$CH$_3$ or CH(CH$_4$)$_2$, it is recommended to react a compound of the formula I$_a$ in which R$_a$ is H with a mixture of formaldehyde and a carboxylic acid of the formula:

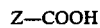 (IV)

in which Z is H, CH$_3$ or CH$_2$CH$_3$ respectively, to give the corresponding N-alkyl derivative in which R$_a$ is CH$_3$, CH$_2$CH$_3$ or CH(CH$_3$)$_2$ respectively.

The reaction with the mixture HCHO+IV (in which the said mixture participates as both solvent and reagent) is carried out at 45°–55° C. until the evolution of $CO_2$ has ended, and then under reflux for at least 1 h. If appropriate, when Y is OH, the reaction may sometimes involve prior blocking of the hydroxyl functional group by means of a suitable protecting group, followed by elimination of this protecting group after the N-alkylation reaction has been carried out.

The N-acylation reaction of stage (b) can be carried out by a method known per se. For example, a compound of the formula I$_a$ in which R$_a$ is H can be reacted with an N-acylating reagent selected in particular from the group comprising the acid halides and anhydrides of the formulae:

 (V)

and

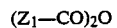 (VI)

in which Z$_1$ is a $C_1$–$C_4$ alkyl group and Hal is a halogen atom, especially F, Cl or Br (the preferred halogen here being Cl).

This N-acylation reaction is advantageously carried out in the presence of a proton acceptor (especially pyridine or picoline, which can also participate as solvents) using proportions of at least 2 mol of halide V or at least 1 mol of anhydride VI per mol of compound I$_a$ in which R$_a$ is H. It can be carried out at room temperature (15°–20° C.), or at a higher temperature, for at least 2 h.

If appropriate, when Y is OH, it may be advantageous to protect the hydroxyl functional group in order to carry out the N-acylation as indicated above for the N-alkylation.

Synthesis of the Compounds of the Formula I$_b$ 1 mol of a 2-phenylpropane-1,3-diamine II is reacted with at least 1 mol of an alkylamidine III$_b$ (preferably 1.5 to 2.5 mol of III$_b$ per mol of II) under reflux in a suitable solvent (especially a $C_1$–$C_3$ lower alkanol, preferably $C_2H_5OH$) until the evolution of NH$_3$ has ended.

Synthesis of the Compounds of the Formula I$_c$ 1 mol of a 2-phenylpropane-1,3-diamine II is reacted with at least 1 mol of a carbonyl compound III$_c$ at room temperature (15°–20° C.) in a suitable solvent (preferably $H_2O$) for at least 3 h (preferably for 3 to 10 h) under atmospheric pressure.

The compounds of the formula I according to the invention share the property of acting on the CNS. In their neuropsychopharmacological profile, they display in particular antidepressant and sedative effects of greater or lesser intensity. More precisely, (i) the compounds of the formula I$_c$ act mainly as sedatives and possess relatively unpronounced antidepressant effects; on the other hand, (ii) the compounds of the formulae I$_a$ and I$_b$ display mainly antidepressant effects on the CNS and, to a minor extent, sedative effects which become apparent at high doses. The compounds of the formula I$_a$ also display peripheral α-adrenergic stimulant properties, as will be seen below. The compounds of the formulae I$_a$ and I$_b$ are particularly valuable in therapy as antidepressant substances.

According to the invention, a therapeutic composition is recommended which contains, in association with a physiologically acceptable excipient, at least one derivative selected from the group comprising the compounds of the formula I and their non-toxic addition salts.

Of course, in a composition of this type, the active principle, namely the compound of the formula I or one of its non-toxic salts, is present in a pharmaceutically effective amount.

According to the invention, to obtain an anti-depressant drug for the CNS with a view to use in human therapy for depressions and depressive states, it is recommended to use a substance selected from the group comprising (i) the 5-phenyl-1,4,5,6-tetrahydropyrimidines of the formulae $I_a$ and $I_b$, and (ii) their non-toxic addition salts.

Also according to the invention, to obtain a sedative drug with a view to use in human therapy for states of hyperexcitation and nervosism, it is recommended to use a substance selected from the group comprising (i) the 5-phenyl-1,2,3,4,5,6-hexahydropyrimidines of the formula $I_c$, and (ii) their non-toxic addition salts.

Further advantages and characteristics of the invention will be understood more clearly from the following description of preparative examples and results of pharmacological tests; these data as a whole do not in any way imply a limitation but are given by way of illustration.

PREPARATION I

Preparation of
1-acetyl-5-phenyl-1,4,5,6-tetrahydropyrimidine hydrochloride

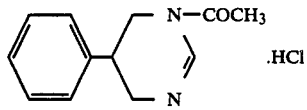

(Example 7; Code No.: CRL 41 378)

40 g (0.186 mol) of 5-phenyl-1,4,5,6-tetrahydropyrimidine hydrochloride hemihydrate are dissolved in water, NaOH is added until the pH is 11 and the free base formed (5-phenyl-1,4,5,6-tetrahydropyrimidine) is collected. After washing with water and then drying in an oven at 60° C., 22.2 g (0.139 mol) of the said free base are dissolved in 555 ml of pyridine, and 14.15 g (0.139 mol) of acetic anhydride are added. The mixture is left to stand at room temperature (15°–20° C.) for 20 h and evaporated to dryness, the evaporation residue is taken up with 100 ml of anhydrous ethanol and acidified with ethanol containing HCl, and the crystals formed are filtered off. Recrystallization from anhydrous ethanol gives 11 g (yield: 33%) of CRL 41 378. M.p. (inst.)=200° C.

PREPARATION II

Preparation of
5-hydroxy-5-phenyl-1,4,5,6-tetrahydropyrimidine hydrochloride

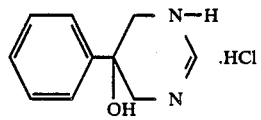

(Example 8; Code No.: CRL 41 382)

A mixture consisting of 5.56 g (0.0335 mol) of 1,3-diamino-2-phenylpropan-2-ol dihydrochloride (m.p. (inst.)=242° C.) and 2.479 g (0.0335 mol; 2.7 ml) of ethyl formate is heated at 100° C. for 3 h. It is then heated at 100° C. under reduced pressure (vacuum obtained by means of a water-jet pump) for 1 h. The reaction medium is cooled, taken up with CH3OH, acidified with ethanol containing HCl and evaporated to dryness, and the evaporation residue is triturated with ether, acetone and chloroform. The precipitate formed is collected by filtration and then recrystallized from an ethanol/diethyl ether mixture (1:1 v/v) to give 6 g (yield: 84%) of CRL 41 382. M.p. (inst.)=206° C.

Analysis { % Cl⁻ measured: 17.04%
         { % Cl⁻ theoretical: 16.70%

PREPARATION III

Preparation of
5-(2-fluorophenyl)-1,4,5,6-tetrahydropyrimidine hydrochloride (Example 6; Code No.: CRL 41 329)

A reaction medium obtained by adding 7.96 ml of ethyl formate to 20 g (0.119 mol) of 2-(2-fluorophenyl)-propane-1,3-diamine is heated at 100° C. for 3 h under atmospheric pressure and then at 150° C. for 1.50 h under reduced pressure (vacuum obtained by means of a water-reduced jet pump). It is cooled, treated with CH3OH, acidified with ethanol containing HCl and evaporated to dryness, and the evaporation residue is triturated with ether, aacetone and then chloroform. The crystals formed are filtered off and recrystallized from a CH3COCH3/ CH3CH2OH mixture (1:1 v/v) to give 10 g (yield: 39%) of CRL 41 329. M.p. (inst.)=210° C.

Analysis { % Cl⁻ measured: 16.50%
         { % Cl⁻ theoretical: 16.55%

PREPARATION IV

Preparation of
2,2-dimethyl-5-(2-fluorophenyl)-1,2,3,4,5,6-hexahydropyrimidine dihydrochloride (Example 22; Code No.: CRL 41 330)

194.6 g (1.22 mol; 62.4 ml) of bromine are run into a solution of 227.8 g of NaOH in 1700 ml of water at −3° C. 122 g of 2-(2-fluorophenyl)propane-1,3-dicarboxamide (m.p. (inst.=206°–208° C.) are added in 5 portions and the mixture is stirred at 0° C. until a clear solution is obtained, at room temperature (15°–20° C.) for 1 hour and then at 70° C. for 0.75 h. It is cooled and extracted with 6 times 200 ml of chloroform.

50 ml of acetone and some magnesium sulfate are added to the resulting chloroform phase [which contains 2-(2-fluorophenyl)propane-1,3-diamine] without washing the said phase with water, and the mixture is then stirred at room temperature (15°–20° C.) overnight. It is filtered, the filtrate is evaporated to dryness, the evaporation residue is taken up with petroleum ether and the crystals formed are then filtered off. The crystals are taken up with petroleum ether under reflux, an insoluble material is filtered off hot, the filtrate is placed in a refrigerator and the precipitate formed is then collected by filtration and dried in vacuo to give 38 g (yield: 41%) of 2,2-dimethyl-5-(2-fluorophenyl)-1,2,3,4,5,6-hexahydropyrimidine.

| Analysis | % N measured: 13.50% |
|---|---|
| | % N theoretical: 13.46% |

The free base obtained in this way is used to form the dihydrochloride. This is done by dissolving the free base in CH$_3$OH and acidifying the solution with ethanol containing HCl. The resulting solution is evaporated and the evaporation residue is dried at 50° C. in vacuo to give 51 g (yield: 99.3%) of CRL 41 330.

PREPARATION V

Preparation of 2,2-dimethyl-5-hydroxy-5-phenyl-1,2,3,4,5,6-hexahydropyrimidine (Example 24; Code No.: CRL 41 365)

(a) 1,3-Dichloro-3-phenylpropan-2-ol 289 ml (0.866 mol) of a 3M solution of phenylmagnesium bromide in ether are run, over a period of 1.50 h, into a solution of 100 g (0.787 mol) of 1,3-dichloroacetone in 1000 ml of anhydrous ether under a nitrogen atmosphere and at −60° C. After 10 minutes, a solution of 83.5 g of acetic acid in 126 ml of ether is added to the reaction medium. The temperature is allowed to rise to +4° C. and 315 ml of water are run in. The ether phase is decanted, washed with water and dried over MgSO$_4$. It is filtered, the filtrate is evaporated to dryness and the evaporation residue is distilled in vacuo to give 82.3 g (yield: 51%) of 1,3-dichloro-2-phenylpropan-2-ol. B.p. (0.5 mm Hg)=102° C. (0.5 mm Hg corresponds to 66.6 Pa).

(b) 1,3-Diphthalimido-2-phenylpropan-2-ol

A mixture of 30.6 g (0.149 mol) of 1,3-dichloro-2-phenylpropan-2-ol, 55.5 g (0.300 mol) of potassium phthalimide and 300 ml of dimethylformamide is heated in a water bath at 100° C. for 4 h. The resulting reaction medium is cooled and evaporated until the volume has been halved, and the insoluble material formed is filtered off, washed with CH$_3$OH and then dried to give 40 g (yield: 63%) of 1,3-diphthalimido-2-phenylpropan-2-ol.

(c) 2-Hydroxy-2-phenylpropane-1,3-diamine dihydrochloride 40 g (0.094 mol) of 1,3-diphthalimido-2-phenylpropan-2-ol are dissolved in 400 ml of a C$_2$H$_5$OH/H$_2$O mixture (95:5 v/v). 10.2 g of hydrazine hydrate are added and the reaction medium is heated under reflux for 2 h. After cooling and acidification with 12N HCl, the insoluble material is filtered off and the filtrate is evaporated to dryness. The evaporation residue is taken up with 50 ml of H$_2$O and 100 ml of CHCl$_3$ and the insoluble material formed is then removed by filtration. The aqueous phase is extracted with 8×50 ml of CHCl$_3$, the organic phases are combined, dried over MgSO$_4$ and filtered (to remove MgSO$_4$) and the filtrate is then evaporated to dryness. The evaporation residue is taken up with ether and the precipitate formed is collected by filtration. Recrystallization from ethanol gives 8 g (yield: 35%) of 2-hydroxy-2-phenylpropane-1,3-diamine dihydrochloride. M.p. (inst.)=242° C.

| Analysis | % Cl$^-$ measured: 29.65% |
|---|---|
| | % Cl$^-$ theoretical: 29.62% |

(d) CRL 41 365

4.4 g (0.01841 mol) of the dihydrochloride obtained in stage (c) above are dissolved in 50 ml of water. 2.2 g of sodium hydroxide pellets and 3 ml of acetone are added. The mixture is left to stand overnight at room temperature (15°–20° C.) and extracted with 3×100 ml of CHCl$_3$, and the chloroform phase is washed with 30 ml of water, dried over MgSO$_4$ and then filtered to remove MgSO$_4$. The filtrate is evaporated to dryness; recrystallization from petroleum ether (fraction boiling at 45°–60° C.) gives 2.6 g (yield: 68.5%) of CRL 41 365. M.p.=108° C.

PREPARATION VI

Preparation of 5-phenyl-1,2,3,4,5,6-hexahydropyrimidine dihydrochloride (Example 28; Code No.: CRL 41 355)

37.5 g (0.168 mol) of 2-phenylpropane-1,3-diamine dihydrochloride are dissolved in 100 ml of water, and 13.52 g (0.336 mol) of sodium hydroxide pellets are added. The mixture is cooled in a bath of water+ice and 17 ml of a 30% (w/v) aqueous solution of formaldehyde are added. The mixture is left overnight at room temperature (15°–20° C.) and extracted with 5×50 ml of CHCl$_3$, and the chloroform phase is washed with 25 ml of water, dried over MgSO$_4$ and filtered. The filtrate is evaporated to dryness, the evaporation residue is taken up with 500 ml of anhydrous C$_2$H$_5$OH and acidified with ethanol containing HCl, and the precipitate formed is collected by filtration, washed with a small quantity of anhydrous ethanol and dried in vacuo to give 24 g (yield: 58%) of CRL 41 365. M.p. (inst.)=192° C.

| Analysis | % Cl$^-$ measured: 29.71% |
|---|---|
| | % Cl$^-$ theoretical: 30.47% |

PREPARATION VII

Preparation of 2-methyl-5-phenyl-1,4,5,6-tetrahydropyrimidine hydrochloride (Example 16; Code No.: CRL 41 352)

A mixture consisting of 20 g (0.0897 mol) of 2-phenylpropane-1,3-diamine dihydrochloride, 10.76 g (0.269 mol) of sodium hydroxide pellets and 8.48 g (0.0897 mol) of acetamidine hydrochloride is heated under reflux until the evolution of NH$_3$ has ended. The reaction medium is cooled, the insoluble material is filtered off and discarded, the filtrate is acidified with ethanol containing HCl and evaporated to half the volume, and the insoluble material formed is filtered off. The filtrate is diluted with an equal volume of ether, the insoluble material formed is filtered off and the resulting filtrate is evaporated to dryness. Recrystallization of the evaporation residue from an acetone/ethanol mixture (1:1 v/v) gives 6 g (yield: 32%) of CRL 41 352. M.p. (inst.)=220° C.

PREPARATION VIII

Preparation of
1-methyl-5-phenyl-1,4,5,6-tetrahydropyrimidine
hydrochloride

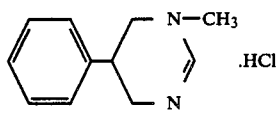

(Example 2; Code No.: CRL 41 337)

21 g (0.102 mol) of 5-phenyl-1,4,5,6-tetrahydropyrimidine hydrochloride hemihydrate are dissolved in water, NaOH is added until the pH is 11 and the insoluble material is filtered off, washed with water and then collected.

12 ml of a 30% (w/v) aqueous solution of formaldehyde and 10.6 ml of 99% (w/v) formic acid are added to the free base obtained in this way (namely 5-phenyl-1,4,5,6-tetrahydropyrimidine). The mixture is heated at 45°–55° C. until the evolution of $CO_2$ has ended, and then under reflux for 4 h. It is evaporated to dryness and the evaporation residue is taken up with water, rendered alkaline with NaOH until the pH is 11, and extracted with ether. The ether phase is washed with water, dried over $MgSO_4$ and filtered (to remove $MgSO_4$) and ethanol containing HCl is added. The resulting ether phase is decanted and the oily residue is placed in a vacuum desiccator in the presence of KOH and $P_2O_5$ for 24 h. The expected hydrochloride crystallizes. 8 g (yield: 37%) of CRL 41 337 are collected.

PREPARATION IX

Preparation of
5-(4-chlorophenyl)-1,4,5,6-tetrahydropyrimidine
hydrochloride

(Example 1; Code No.: CRL 41 336)

30 g (0.1165 mol) of 2-(4-chlorophenyl)propane-1,3-diamine dihydrochloride are dissolved in the minimum quantity of water, NaOH is added until the pH is 11, the mixture is extracted with 4×100 ml of chloroform, the chloroform phase is washed with 50 ml of water, dried over $MgSO_4$ and filtered, and the filtrate is evaporated to dryness to give 20.8 g (0.1127 mol) of 2-(4-chlorophenyl)propane-1,3-diamine.

8.34 g (0.1127 mol; 9.1 ml) of ethyl formate are added to the free base obtained in this way. The reaction medium is heated at 90°–100° C. for 3 h under atmospheric pressure and then at 150°–155° C. for 1.50 h under reduced pressure (water-jet pump). It is cooled, methanol is added and the mixture is acidified with ethanol containing HCl and evaporated to dryness. The evaporation residue is taken up with $CH_3COCH_3$ and the crystals formed are filtered off. Recrystallization of these crystals from a $CH_3COCH_3/C_2H_5OH$ mixture (1:1 v/v) gives 10 g (yield: 38%) of CRL 41 336. M.p. (inst.)=226°–230° C.

The results of toxicological and neuropsychopharmacological tests which were carried out with the products according to the invention have been summarized below. In these tests, solutions of the said products in distilled water were administered intraperitoneally in a volume of 20 ml/kg to male mice and in a volume of 5 ml/kg to male rats.

A. TESTS RELATING TO CRL 41 378 (Ex. 7)

The tests were carried out in solution in water at pH 4.0–5.5. The pH of the aqueous solution of CRL 41 378 varies according to the concentration: it is 4.0 at a concentration of 50 g/l, 4.5 at 12.5 g/l, 5.0 at 0.8 g/l and 5.5 at CRL 41 378 concentrations less than or equal to 0.2 g/l.

I. TOXICITY

In male mice (groups of three animals per dose), the $LD_O$ (maximum non-lethal dose) of CRL 41 378 by intraperitoneal administration is greater than 256 mg/kg, at which dose all the animals treated exhibit dyspnea, substantial salivation and convulsions 10 minutes after administration.

II. OVERALL BEHAVIOR AND REACTIVITIES

Groups of 3 animals are observed before and then 0.25 h, 0.50 h, 1 h, 2 h, 3 h and 24 h after the administration of CRL 41 378. The following observations are made:

(1) in mice at a dose of 1 mg/kg:
no distinct modification of the behavior and reactivities compared with the control animals;

at a dose of 4 mg/kg:
moderate mydriasis for 3 h, the maximum intensity being reached 1 h after administration;

at a dose of 16 mg/kg:
moderate salivation 1 h after administration,
moderate hypothermia, and
moderate mydriasis 1 h after administration; and at a dose of 64 mg/kg:
sedation for 3 h,
a decrease in the breathing rate appearing between T+0.5 h and T+1 h after administration,
moderate hypothermia,
an increase in the reactivity to touch and vasodilation of the paws for 0.5 h,
salivation appearing between T+1 h and T+2 h after administration, and
mydriasis for 3 h; and (2) in rats at a dose of 0.5 mg/kg:
moderate mydriasis for 2 h, the maximum intensity being reached 0.5 h after administration;

at a dose of 2 mg/kg:
mydriasis for 3 h, the maximum intensity also being reached 0.5 h after administration; and at a dose of 32 mg/kg:
a decrease in the breathing rate and muscle tonus for 1 h,
exophthalmos for 1 h,
piloerection for 2 h,
salivation appearing 0.5 h after administration,
vasodilation of the paws and snout for 0.5 h, and
mydriasis for 2 h, the maximum intensity being reached 0.5 h after administration.

III. INTERACTION WITH APOMORPHINE (1) In mice

CRL 41 378 is administered to groups of 6 mice 30 minutes before the subcutaneous injection of 1 or 16 mg/kg of apomorphine. It is observed that, as from a dose of 0.5 mg/kg, CRL 41 378 antagonizes the hypothermia induced by apomorphine and that it causes practically no modification of the righting behavior and stereotypies due to apomorphine.

(2) In rats

CRL 41 378 is administered to groups of 12 rats 0.5 h before the subcutaneous injection of 0.5 mg/kg of apomorphine. It is observed that, at the two highest doses used (8 and 32 mg/kg), CRL 41 378 seems to cause a moderate decrease in the stereotypies induced by apomorphine.

IV. INTERACTION WITH AMPHETAMINE

Amphetamine (2 mg/kg) is injected intraperitoneally into groups of 6 rats 30 minutes after the administration of CRL 41 378. It is found that, at the highest dose used (32 mg/kg), CRL 41 378 potentiates the stereotypies induced by amphetamine.

V. INTERACTION WITH RESERPINE

Four hours after the intraperitoneal injection of 2.5 mg/kg of reserpine, groups of 12 mice receive CRL 41 378. It is noted that, at doses of 0.5 mg/kg to 4 mg/kg, CRL 41 378 antagonizes the hypothermia induced by reserpine and that this effect tends to decrease to nothing at a dose of 16 mg/kg, the highest dose used (64 mg/kg) being inactive towards the hypothermia induced by reserpine. It is furthermore observed that, as from a dose of 0.5 mg/kg, CRL 41 378 causes a moderate decrease in the ptosis induced by reserpine 24 h after administration.

VI. INTERACTION WITH OXOTREMORINE

CRL 41 378 is administered to groups of 6 mice 0.5 h before the intraperitoneal injection of 0.5 mg/kg of oxotremorine.

(1) Action on the temperature

It is found that, as from the lowest dose (0.5 mg/kg), CRL 41 378 antagonizes the hypothermic action of oxotremorine. This antagonism is very intense at doses of 2 and 4 mg/kg and is then less significant for the highest doses used (16 and 64 mg/kg).

(2) Action on the trembling

It is found that CRL 41 378 does not modify the intensity of the trembling induced by oxotremorine.

(3) Action on the peripheral cholinergic symptoms

It is observed that CRL 41 378 causes practically no modification of the signs of peripheral cholinergic stimulation induced by oxotremorine.

VII. ACTION ON THE FOUR PLATE TEST, TRACTION AND ELECTRIC SHOCK

The test is performed on groups of 10 mice 30 minutes after the administration of CRL 41 378.

It is found that CRL 41 378 does not modify the number of punished passes and that it does not cause motor incoordination. At the two highest doses studied (16 and especially 64 mg/kg), CRL 41 378 strongly aggravates the lethal effects of electric shock without modifying the convulsant effects.

VIII. ACTION ON THE SPONTANEOUS MOTILITY 0.5 h after they have received CRL 41 378, the mice (6 per dose, 12 control animals) are placed in an actimeter, where their motility is recorded for 30 minutes.

It is observed that, at a dose of 16 mg/kg and especially at a dose of 64 mg/kg, CRL 41 378 decreases the spontaneous motor activity of the mice.

IX. ACTION ON THE INTERGROUP AGGRESSIVENESS

After they have stayed for 3 weeks in the two halves of a cage divided by an opaque partition, groups of 3 mice receive CRL 41 378. Half an hour later, the two groups from the same cage are brought together by removal of the partition and the number of fights which occur in 10 minutes is noted. It is found that CRL 41 378 decreases the intergroup aggressiveness as from a dose of 0.5 mg/kg but especially at doses of 2 mg/kg, 4 mg/kg and 16 mg/kg.

X. ACTION TOWARDS SOME FORMS OF BEHAVIOR PERTURBED BY VARIOUS AGENTS (1) Motility reduced by habituation to the enclosure After they have stayed in the actimeters for 18 hours, the mice (6 per dose, 12 control animals) receive CRL 41 378. They are immediately returned to their respective enclosures and, half an hour later, their motility is recorded for 30 minutes. It is found that CRL 41 378 does not cause a resumption in the motor activity of mice accustomed to their enclosure.

(2) Motility reduced by hypoxic aggression 0.5 h after they have received CRL 41 378, the mice (10 per dose, 20 control animals) are subjected to acute hypobaric anoxia [pressure reduction of 600 mm Hg (i.e. about $8 \times 10^4$ Pa) in 90 seconds, followed by release of vacuum in 45 seconds] and are then placed in an actimeter, where their motility is recorded for 10 minutes.

It is observed that, at doses of 1 mg/kg, 4 mg/kg and 16 mg/kg, CRL 41 378 does not cause a modification of the motor recovery of mice whose motility has been depressed following a brief period in a reduced-pressure enclosure. At a dose of 64 mg/kg, CRL 41 378 aggravates the effects of hypobaric anoxia and causes the death of all the animals treated.

(3) Asphyxiant anoxia

Groups of 10 mice receive CRL 41 378 30 minutes before the intraperitoneal administration of 32 mg/kg of gallamine triiodoethylate (reference curarizing agent). It is observed that, at the highest dose used (64 mg/kg), CRL 41 378 causes a moderate decrease in the time taken for convulsions and death to occur following asphyxiant anoxia caused by a curarizing agent.

XI. INTERACTION WITH BARBITAL

Half an hour after the administration of CRL 41 378, groups of 10 mice receive an intraperitoneal injection of barbital (220 mg/kg). It is found that CRL 41 378 causes practically no modification of the duration of the sleep induced by barbital.

XII. ACTION ON THE "BEHAVIORAL DESPAIR"

Half an hour after they have received CRL 41 378, groups of 6 mice are placed in a beaker filled with water to a height of 6 cm. The total period of immobility between the 2nd and 6th minutes following immersion is noted. It is observed that CRL 41 378 causes a moderate decrease in the period of immobility of mice which have been forcibly immersed.

XIII. CONCLUSIONS

The results of the tests undertaken show that, in its neuropsychopharmacological profile, CRL 41 378 has:

antidepressant effects appearing as from the lowest doses and illustrated on the one hand by antagonism of the hypothermia induced by apomorphine, reserpine and oxotremorine in mice (although this antagonism is less significant or even non-existent for the highest doses used), and on the other hand by moderate antagonism of the "behavioral despair" in mice;

sedative effects appearing at high doses and represented by:
 sedation in mice,
 a substantial decrease in the spontaneous motor activity of mice,
 a decrease in the intergroup aggressiveness of mice (at doses which do not decrease the spontaneous motor activity), and
 moderate antagonism of the stereotyped movements induced by apomorphine in rats; and peripheral α-adrenergic stimulant effects appearing at high doses, especially as:
 an $\alpha_1$ stimulation component represented by salivation and mydriasis (in mice and rats) and piloerection (in rats),
 moderate hyperthermia in mice, and
 peripheral vasodilation (tail, paws and snout) in mice and rats.

Furthermore, it is found that CRL 41 378 aggravates the lethal effects of the various convulsants studied (electric shock, hypobaric hypoxia, asphyxiant anoxia).

In summary, CRL 41 378 was shown to be an antidepressant exhibiting sedative effects at high doses. It resembles β-adrenergic stimulants and differs from (i) imipramine antidepressants by the absence of peripheral anticholinergic activity and the absence of significant antagonism of the immobility due to despair, (ii) stimulant antidepressants, such as nomifensin and amineptin or even amphetamine, by the, absence of stimulant effects on the CNS, and (iii) monoamine oxidase inhibitors by the absence of distinct antagonism of the ptosis induced by reserpine, on the one hand, and the speed at which its effects appear, on the other.

B. TESTS RELATING TO CRL 41 382 (Ex. 8)

Using the procedures given above, the following results were obtained with a solution of CRL 41 382 in water at pH 6.

I. TOXICITY

In male mice, the $LD_0$ of CRL 41 382 by intraperitoneal administration is greater than 256 mg/kg and the $LD_{60}$ is of the order of 500 mg/kg.

II. OVERALL BEHAVIOR AND REACTIVITIES

The following observations are made:
(1) in mice
at doses of 1 mg/kg, 4 mg/kg and 16 mg/kg:
 no distinct modification of the behavior and reactivities compared with the control animals receiving only distilled water; and
at a dose of 64 mg/kg:
 sedation for 1 h, and
 a decrease in the reactivity to touch and the fear reaction for 0.5 h; and
(2) in rats
at doses of 0.5 mg/kg, 2 mg/kg and 8 mg/kg:
 behavior, reactivities and variations in the pupil diameter and rectal temperature which are analogous to those of the control group; and
at a dose of 32 mg/kg:
 moderate mydriasis for 1 h.

III. INTERACTION WITH APOMORPHINE

In mice, as from a dose of 1 mg/kg and especially at doses of 16 to 64 mg/kg, CRL 41 382 opposes the hypothermia induced by apomorphine, but it causes practically no modification of the righting behavior and stereotypies.

In rats, CRL 41 382 causes practically no modification of the stereotypies induced by apomorphine.

IV. INTERACTION WITH AMPHETAMINE

In mice, CRL 41 382 causes practically no modification of the stereotypies induced by amphetamine.

V. INTERACTION WITH RESERPINE

At doses of 4 mg/kg and 16 mg/kg, CRL 41 382 opposes the hypothermia induced by reserpine. At the highest dose used (64 mg/kg), CRL 41 382 has no effect on the hypothermia induced by reserpine.

Furthermore, it is found that CRL 41 382 causes practically no modification of the ptosis induced by reserpine.

VI. INTERACTION WITH OXOTREMORINE

As from a dose of 1 mg/kg, CRL 41 382 opposes the hypothermia induced by oxotremorine; the antagonism is very intense at a dose of 64 mg/kg.

CRL 41 382 causes practically no modification of the trembling or the signs of peripheral cholinergic stimulation due to oxotremorine.

VII. ACTION ON THE FOUR PLATE TEST, TRACTION AND ELECTRIC SHOCK

CRL 41 382 causes practically no modification of the number of punished passes. It does not cause major motor incapacity. It does not oppose the convulsant effects but it aggravates (at a dose of 64 mg/kg) the lethal effects of electric shock.

VIII. ACTION ON THE SPONTANEOUS MOTILITY

CRL 41 382 does not modify the spontaneous motor activity of mice.

IX. ACTION ON THE INTERGROUP AGGRESSIVENESS

In mice, it is observed that CRL 41 382 causes practically no modification of the number of fights.

X. ACTION TOWARDS SOME FORMS OF BEHAVIOR PERTURBED BY VARIOUS AGENTS (1) Motility reduced by habituation to the enclosure
CRL 41 382 does not cause a resumption in the motor activity of mice accustomed to their enclosure.
(2) Motility reduced by hypoxic aggression
At doses of 16 mg/kg and 64 mg/kg, CRL 41 382 causes an increase in the motor recovery of mice whose motility has been decreased following a brief period in a reduced-pressure enclosure.

(3) Asphyxiant anoxia

CRL 41 382 causes practically no modification of the time taken for convulsions and death to occur following anoxia caused by a curarizing agent such as gallamine triiodoethylate.

XI. INTERACTION WITH BARBITAL

It is found that CRL 41 382 causes practically no modification of the duration of the sleep induced by barbital.

XII. ACTION ON THE "BEHAVIORAL DESPAIR"

It is observed that CRL 41 382 does not modify the period of immobility of mice which have been forcibly immersed.

XIII. CONCLUSIONS

The results of the tests summarized above show that, in its neuropsychopharmacological profile, CRL 41 382 has:

antidepressant effects appearing as from the lowest doses used and illustrated by antagonism of the hypothermia induced by apomorphine, oxotremorine and reserpine in mice (although antagonism of the hypothermia induced by reserpine no longer appears at the high dose of CRL 41 382 used); and sedative effects appearing transiently at the highest doses used (with no detectable decrease in the motor activity).

The beneficial fact that CRL 41 382 causes a moderate increase in the motor recovery of mice after acute hypobaric hypoxia, in the absence of any motor stimulation, even if frustrated, and in the absence of any anticonvulsant action, is currently unexplained.

In summary, CRL 41 382 is a very active antidepressant having a low-intensity sedative component at high doses.

The general profile of the activity of CRL 41 382 in animals makes this substance resemble β-adrenergic stimulants. In fact, the absence of peripheral anticholinergic activity and the absence of antagonism of the immobility due to "despair" distinguish CRL 41 382 from imipramine antidepressants. The absence of stimulant effects distinguishes CRL 41 382 from stimulant antidepressants such as nomifensin, amineptin or even amphetamine. Finally, the absence of antagonism of the ptosis induced by reserpine and the speed with which the effects of CRL 41 382 appear enable it to be distinguished from monoamine oxidase inhibitors.

C. TESTS RELATING TO CRL 41 329 (Ex. 6)

Using the procedures given above, the following results were obtained for a solution of CRL 41 329 in water at pH 6, administered intraperitoneally.

(a) Toxicity

In male mice, the $LD_0$ (maximum non-lethal dose) of CRL 41 329 by intraperitoneal administration is greater than 64 mg/kg, at which dose all the animals treated exhibit salivation, sedation and vasodilation of the tail, and the $LD_{100}$ (minimum dose lethal to all the animals) is of the order of 128 mg/kg, at which dose all the animals have asphyxiant convulsions 10 to 15 minutes after administration, death occurring in 15 to 25 minutes.

(b) Overall behavior and reactivities

The following observations are made:
(1) in mice
at a dose of 0.5 mg/kg:
moderate mydriasis for 2 h;
at a dose of 2 mg/kg:
sedation (2 out of 3 animals) for 0.5 h, and moderate and brief mydriasis for 0.5 h;
at a dose of 8 mg/kg:
sedation (2 out of 3 animals) for 0.5 h, and weak and brief mydriasis for 0.5 h; and
at a dose of 32 mg/kg:
sedation (3/3) 0.25 h after administration, then (2/3) 0.5 h after administration; and
(2) in rats
at a dose of 0.25 mg/kg:
moderate mydriasis for 3 h;
at a dose of 1 mg/kg:
significant mydriasis for 3 h;
at a dose of 4 mg/kg:
sedation (3/3) for 2 h,
a decrease in the reactivity to touch and the muscle tone,
piloerection (¼) for 1 h, and
significant mydriasis for at least 3 h (mydriasis still being apparent 24 h after administration); and
at a dose of 16 mg/kg:
sedation (3/3) for 3 h,
a decrease in the reactivity to touch and the muscle tone, and
significant mydriasis for 3 h (the mydriasis still being apparent 24 h after administration).

(c) Results of the neuropsychopharmacological tests

It is found that, in its neuropsychopharmacological profile, CRL 41 329 has:

antidepressant effects appearing at all the doses used and illusrated by significant antagonism of the hypothermia induced by apomorphine, oxotremorine and reserpine (with no decrease in the period of immobility due to "despair"); and sedative effects appearing at high doses and represented by:
sedation with hypomotility,
a decrease in the motor recovery after hypoxic aggression,
a decrease in the intergroup aggressiveness in mice, and
low-intensity transient hypothermia.

It is also observed that CRL 41 329 additionally exhibits modest effects capable of reflecting peripheral α-adrenergic stimulation, on the one hand, and causes aggravation of the lethal effects of electric shock and gallamine triiodoethylate in mice, on the other. Paradoxically, it potentiates the stereotypies induced by amphetamine.

D. TESTS RELATING TO CRL 41 352 (Ex. 16)

Using the procedures given above, the results summarized below were obtained for a solution of CRL 41 352 in water at pH 5.5, administered intraperitoneally.

(a) Toxicity

In male mice, the $LD_0$ of CRL 41 352 by intraperitoneal administration is greater than 64 mg/kg, at which dose all the animals treated exhibit sedation and a decrease in the breathing rate. The $LD_{30}$ is of the order of 128 mg/kg.

(b) Overall behavior and reactivities

At doses of 0.5 mg/kg, 2 mg/kg, 8 mg/kg and 32 mg/kg, no distinct modification of the behavior and reactivities is observed in mice. In rats, on the other hand, mydriasis is observed at doses of 4 mg/kg and 16 mg/kg and a decrease in the breathing rate is observed at a dose of 16 mg/kg.

(c) Results of the neuropsychopharmacological tests

It is found that, in its neuropsychopharmacological profile, CRL 41 352 has:

antidepressant effects which are very distinct, represented by significant antagonism (as from the lowest doses used) of the hypothermia induced by apomorphine and oxotremorine, on the one hand, and more moderate antagonism of the hypothermia induced by reserpine, on the other, but with no decrease in the period of immobility due to "despair";

a stimulant effect which is very moderate, appearing at high doses and represented by a resumption in the motor activity of mice accustomed to their enclosure; and sedative effects appearing at very high doses and illustrated by a decrease in the number of fights in the intergroup aggressiveness test.

In summary, CRL 41 352 has been shown to be principally an antidepressant having a very slight stimulant component and a very weak sedative component.

E. TESTS RELATING TO CRL 41 365 (Ex. 24)

Using the procedures given above, the results summarized below were obtained for a solution of CRL 41 365 in water at pH 5.5, administered intraperitoneally.

(a) Toxicity

In male mice, the $LD_0$ (maximum non-lethal dose) by intraperitoneal administration is greater than 512 mg/kg.

(b) Overall behavior and reactivities

The following observations are made:

(1) in mice at doses of 16 and 64 mg/kg:

no distinct modification of the behavior and reactivities compared with the control animals receiving only distilled water; and at a dose of 256 mg/kg:

sedation, for 1 h, a decrease in the heart rate for 1 h, a decrease in the reactivity to touch for 0.5 h, and hypothermia for 3 h, which reaches its maximum intensity ($-1.6°$ C.) 0.5 h after administration; and (2) in rats at a dose of 8 mg/kg:

no distinct modification of the behavior and reactivities compared with the control animals;

at a dose of 32 mg/kg:

sedation and a decrease in the breathing rate for 1 h, and a decrease in the reactivity to touch for 0.5 h; and at a dose of 128 mg/kg:

sedation and a decrease in the breathing rate for 3 h, and a decrease in the reactivity to touch for 1 h.

(c) Results of the neuropsychopharmacological tests

As regards the tests which were carried out using the procedures given above, CRL 41 365 has been shown to be essentially a sedative (sedation with a decrease in the reactivities in rats and mice, hypothermia in mice, a very moderate decrease in the period of immobility of mice which have been forcibly immersed).

Furthermore, at all the doses studied, this product potentiates the stereotypies induced by amphetamine (the nature of this potentiation probably being pharmacokinetic).

F. TESTS RELATING TO CRL 41 336 (Ex. 1)

I. TOXICITY

In male mice, the $LD_0$ (maximum non-lethal dose) of CRL 41 336 by intraperitoneal administration is greater than 64 mg/kg, at which dose all the animals treated exhibit sedation and a decrease in the breathing rate, and the $LD_{100}$ (minimum dose lethal to all the animals) is of the order of about 200–210 mg/kg, death occurring 10 to 13 minutes after administration.

In male mice, the $LD_{60}$ by intraperitoneal administration is of the order of about 128 mg/kg. At this dose, the animals exhibit sedation and a decrease in the breathing rate, death occurring 24 h after administration for 60% of the animals.

II. OVERALL BEHAVIOR AND REACTIVITIES

Groups of 3 animals are observed before and then 0.25 h, 0.50 h, 1 h, 2 h, 3 h and 24 h after the administration of CRL 41 329. The following observations are made:

(1) in mice at doses of 0.5 to 8 mg/kg:

no distinct modification of the behavior and reactivities; and at a dose of 32 mg/kg:

sedation for 0.25 h, a decrease in the breathing rate from 1 to 3 hours, moderate hypothermia ($-1.3°$ C.) from 1 to 3 hours, and vasodilation of the ears and tail from 0.5 h to 3 h; and (2) in rats at doses of 0.25 and 1 mg/kg:

behavior, reactivities and variations in rectal temperature and pupil diameter which are substantially comparable to those of the animals in the control group;

at a dose of 4 mg/kg:

mydriasis for 2 hours (maximum 0.5 h after administration); and at a dose of 16 mg/kg:

sedation for 3 h, a decrease in the breathing rate for 3 h, mydriasis for 3 h (with its maximum intensity 0.5 h after administration), piloerection for 1 h, and vasodilation (of the paws) for 2 h.

III. NEUROPSYCHOPHARMACOLOGICAL STUDY

The results of the tests undertaken show that, in its neuropsychopharmacological profile, CRL 41 336 has:

antidepressant effects illustrated by distinct antagonism of the hypothermia induced by apomorphine and oxotremorine, on the one hand, and more moderate antagonism of the hypothermia induced by reserpine, on the other;

sedative effects represented by:

sedation in mice and rats, a decrease in the spontaneous motor activity, a decrease in the motility after acute hypobaric hypoxia [pressure reduction of 600 mm Hg (i.e. about $8 \times 10^4$ Pa) in 90 seconds, followed by release of vacuum in 45 seconds] in mice, a decrease in the intergroup aggressiveness in mice, and hypothermia (transient) in mice; and peripheral α-adrenergic stimulant effects appearing at high doses, especially as mydriasis and piloerection in rats.

It is observed that, at high doses, CRL 41 336 (i) causes aggravation of the lethal effect of electric shock, and (ii) decreases the stereotypies induced by apomorphine in rats and mice. The decrease in the stereotypies induced by apomorphine suggests that the mode of action of CRL 41 336 may be of the postsynaptic antidopaminergic type.

G. TESTS RELATING TO CRL 41 337 (Ex. 2)

I. TOXICITY

In male mice, the $LD_0$ of CRL 41 337 by intraperitoneal administration is greater than 256 mg/kg, the $LD_{60}$ is of the order of about 500 mg/kg and the $LD_{100}$ is less than or equal to about 1000 mg/kg.

II. OVERALL BEHAVIOR AND REACTIVITIES

Using the procedures given above, the following observations are made:

(1) in mice
at doses of 2 to 32 mg/kg:
no distinct modification of the behavior and reactivities compared with the control animals; and
at a dose of 128 mg/kg:
moderate hypothermia ($-1.6°$ C. one hour after administration) for 3 h; and (2) in rats
at doses of 1 and 4 mg/kg:
no distinct modification of the behavior and reactivities compared with the control animals; and
at doses of 16 and 64 mg/kg:
mydriasis.

III. NEUROPSYCHOPHARMACOLOGICAL STUDY

The results of the tests undertaken show that, in its neuropsychopharmacological profile, CRL 41 337 has:

antidepressant effects appearing as antagonism of the hypothermia induced by apomorphine, reserpine and oxotremorine, with no modification of the period of immobility due to despair;

sedative effects represented by:
a decrease in the motor activity,
a decrease in the intergroup aggressiveness, and
hypothermia; and peripheral α-adrenergic stimulant effects appearing as:
mydriasis in rats, and
antagonism of the ptosis induced by reserpine.

It is furthermore observed that, at high doses, CRL 41 337 paradoxically causes an improvement in the motor recovery of mice after acute hypobaric hypoxia and a resumption in the motor activity of mice accustomed to their enclosure. In addition, at a high dose, CRL 41 337 causes aggravation of the lethal effects of electric shock.

In summary, as regards the results of the tests undertaken, CRL 41 337 behaves like a substance which acts principally as an antidepressant. Certain aspects of its neuropsychopharmacological profile resemble those of β-adrenergic stimulants (antagonism of the hypothermia induced by apomorphine, reserpine and oxotremorine, but with no effect in the test for measuring the immobility due to despair). Finally, CRL 41 337 differs from imipramine substances by the fact that it has no anticholinergic action and no effect on the immobility due to despair, on the one hand, and from antidepressants, such as nomifensin, by the fact that it exhibits no stimulation of the spontaneous motor activity, on the other.

H. COMPLEMENTARY TESTS

Complementary tests were undertaken with CRL 41 329 (Example 6), CRL 41 378 (Example 7), CRL 41 382 (Example 8) and CRL 41 352 (Example 16), these being the most valuable products according to the invention. These tests related to:

the study of the neuropsychopharmacological properites by gastric administration, the study of the cardiovascular properties by intraduodenal and/or intravenous administration, and the study of the interaction with 5-hydroxytryptophan in mice treated beforehand with a monoamine oxidase inhibitor (MAOI).

1. Neuropsychopharmacological Study by Gastric Administration

Each test product is administered gastrically to male mice, in a volume of 20 ml/kg, 0.50 h before the subcutaneous injection of 16 mg/kg of apomorphine. The purpose of this procedure is to verify the presence or absence of antidepressant effects by gastric administration through interaction with apomorphine.

It is observed that, as from doses of 0.25 mg/kg (CRL 41 329), 0.50 mg/kg (CRL 41 378 and CRL 41 352) and 2 mg/kg (CRL 41 382), the products studied oppose the hypothermia induced by apomorphine. The antagonism of the hypothermia induced by apomorphine increases with the dose of each test product.

It is found that, by gastric administration, a significant effect of the antidepressant type appears for each of the test products and that this effect is similar to that observed after the intraperitoneal administration of the said products.

2. Cardiovascular Study

Groups of 2 adult dogs (each weighing 10 to 18 kg), anesthetized with nembutal, receive each test product (i) by intraduodenal administration at successive doses of 0.1 mg/kg, 0.5 mg/kg, 1 mg/kg, 2.5 mg/kg, 5 mg/kb, 10 mg/kg and 20 mg/kg, and then (ii) if appropriate, by intravenous administration at a dose of 10 mg/kg. The effects of 10 μg/kg of isoprenaline and/or 2 μg/kg of norepinephrine after the intraduodenal administration of a cumulative dose of 39.1 mg/kg are also assessed.

The following are measured: the total arterial blood pressure, the diastolic arterial blood pressure, the heart rate, the blood flows through the femoral and cerebral arteries and saphenous veins, the rectal temperature, the skin temperature and the pressure of the gases (essentially $O_2$) dissolved in the arterial blood.

The following observations are made:

(a) CRL 41 329 (Ex. 6), administered intraduodenally, tends to increase the arterial blood pressure and decrease the heart rate, causing respiratory arrhythmia, and decreases the blood flows in the femoral and vertebral arteries in anesthetized dogs; it causes mydriasis and substantial salivation and increases the rectal temperature and skin temperature; it does not cause a distinct modification of the effects of isoprenaline on the diastolic arterial blood pressure and the heart rate, but it decreases the hypertension induced by norepinephrine.

(b) CRL 41 378 (Ex. 7), administered to anesthetized dogs, has no effect on the arterial blood pressure by intraduodenal administration and is hypotensive by intravenous administration; it decreases the blood flows through the femoral and vertebral arteries; it increases the rectal temperature but does not cause a distinct modification of the skin temperature; it decreases the effects of isoprenaline on the heart rate and decreases the hypertension induced by norepinephrine.

(c) CRL 41 382 (Ex. 8), administered intraduodenally to anesthetized dogs, is hypertensive but has practically no effect on the heart rate; it decreases the blood flows through the femoral and vertebral arteries and also the skin temperature, but it increases the rectal temperature; by intravenous administration, it is hypotensive and bradycardic and decreases the blood flows through the femoral and vertebral arteries; it does not modify the effects of isoprenaline and increases the hypertension caused by norepinephrine; according to these tests, CRL 41 382 seems to have an α-adrenergic stimulant effect.

3. Interaction with 5-hydroxytryptophan

The purpose of the procedure used is to investigate the activity of each product according to the invention as regards the trembling induced by 5-hydroxytryptophan (5-HTP) in association with an MAOI (in this case nialamide).

Each test product, in solution in distilled water, is administered intraperitoneally in a volume of 20 ml/kg to male mice.

Groups of 10 mice receive nialamide (20 mg/kg, administered gastrically) at time T-18 h, each test product at time T-0.5 h and then (±)-5-HTP (20 mg/kg, administered intraperitoneally) at time T. Immediately after the injection of the (±)-5-HTP, the mice are individually placed in transparent plastic boxes. The generalized trembling, the partial trembling and the head twitches are noted on a yes/no basis for 2 h.

It is observed that (i) as from a dose of 1 mg/kg, CRL 41 378 distinctly potentiates the partial trembling and moderately potentiates the head twitches, the potentiation being very intense as from a dose of 16 mg/kg; (ii) as from a dose of 2 mg/kg, CRL 41 329 and CRL 41 352 distinctly potentiate the partial trembling and the head twitches, the potentiation being very intense at the doses of 8 to 32 mg/kg which were studied; and (iii) CRL 41 382 causes a moderate potentiation of the partial trembling and causes practically no modification of the head twitches.

Using this procedure, it is found that the test products differ in their neuropsychopharmacological profiles from tricyclic antidepressants (such as desipramine), amphetamines (such as amphetamine itself) and serotonin release agents (such as fenfluramine), which potentiate all the effects of 5-HTP in the presence of an MAOI. On the other hand, the said products more closely resemble β-adrenergic stimulants, which exert disparate effects towards 5-HTP, such as isoprenaline (distinct potentiation of the trembling and head twitches), fenoterol (distinct potentiation of the trembling and moderate potentiation of the head twitches), ritodrine and, to a lesser extent, salbutamol (moderate potentiation of the trembling but no modification of the head twitches) and terbutaline and ociprenaline (no modification of the trembling or head twitches).

More precisely, using the said procedure, CRL 41 329 and CRL 41 352 have effects analogous to those of isoprenaline, CRL 41 378 more closely resembles fenoterol and CRL 41 382 more closely resembles ritodrine or salbutamol.

Furthermore, it has been observed that the compounds according to the invention, especially CRL 41 329, CRL 41 378, CRL 41 382 and CRL 41 352, are devoid of harmful teratogenic effects on pregnant rabbits.

The clinical trials which have been undertaken have made it possible to determine that the daily dose to be administered orally to adults, in the treatment of depressions and depressive states, is generally between 3 and 120 mg for the products of the formulae $I_a$ and $I_b$ according to the invention.

In particular, excellent results have been obtained in human therapy by the daily oral administration to adults of (i) 2 to 3 tablets or gelatin capsules each containing 25 to 35 mg of CRL 41 378 or CRL 41 382, (ii) 2 to 3 tablets or gelatin capsules each containing 30 mg of CRL 41 329, and (iii) 2 tablets each containing 1.5 to 3 mg of CRL 41 352. In ambulant patients having a depressive symptomatology manifesting itself as asthenia, slowing down or both psycho-intellectual and motor inhibition, CRL 41 352 has proved particularly effective.

As regards the products of the formula $I_c$, which have been found in clinical trials to be of value as sedatives, the recommended daily adult dosage for states of hyperexcitation and nervosism is of the order of 300 to 2000 mg, administered orally.

What is claimed is:

1. A method for the treatment of depression and depressive states, which comprises administering to human being in need of such treatment; A CNS - antidepressant effective amount of at least one substance selected from the group consisting of:

(i) the substituted 5-phenyl-1,4,5,6-tetrahydropyrimidines of the formula:

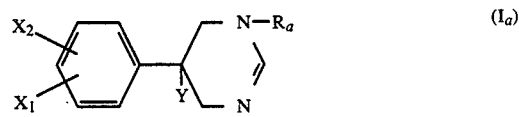

(I$_a$)

in which:

$X_1$ and $X_2$, which are identical or different, each represent H, F, Cl, Br or CF$_3$, Y is H or OH, and $R_a$ is a $C_1$–$C_4$ alkyl group or a $C_2$–$C_5$ alkanoyl group, it being possible for $R_a$ to represent the hydrogen atom when at least one of the groups $X_1$, $X_2$ and Y is different from H;

(ii) the 2-alkyl-5-phenyl-1,4,5,6-tetrahydropyrimidines of the formula:

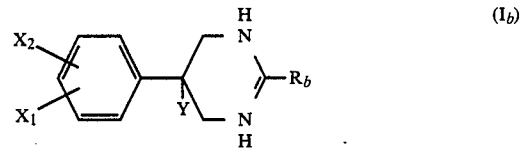

(I$_b$)

in which:

$X_1$ and $X_2$, which are identical or different, each represent H, F, Cl, Br or CF$_3$, Y is H or OH, and $R_b$ is a $C_1$–$C_3$ alkyl group; and (iii) their non-toxic addition salts.

2. The method according to claim 1, which comprises administering a CNS- antidepressant effective amount of at least one substance selected from the group consisting of:

(i) the substituted 5-phenyl-1,4,5,6-tetrahydropyridines of the formula:

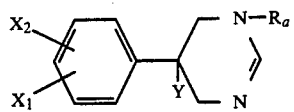
(Ia)

in which:
$X_1$ and $X_2$, which are identical or different, each represent
H, F, Cl, Br or $CF_3$,
Y is H or OH, and
$R_a$ is a $C_1$–$C_4$ alkyl group or a $C_2$–$C_5$ alkanoyl group, it being possible for $R_a$ to represent the hydrogen atom when at least one of the groups $X_1$, $X_2$ and Y is different from H; and (ii) their non-toxic addition salts.

3. The method according to claim 1, which comprises adminstering, a CNS- antidepressant effective amount of at least one substance selected from the group consisting of:

(i) the 2-alkyl-5-phenyl-1,4,5,6-tetrahydropyrimidines of the formula:

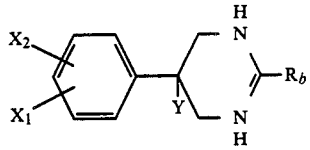
(Ib)

in which:
$X_1$ and $X_2$, which are identical or different, each represent
H, F, Cl, Br or $CF_3$,
Y is H or OH, and
$R_b$ is a $C_1$–$C_3$ alkyl group; and (ii) their non-toxic addition salts.

* * * * *